US007709431B2

(12) United States Patent
Mercurio et al.

(10) Patent No.: US 7,709,431 B2
(45) Date of Patent: May 4, 2010

(54) SOLID DISPERSIONS COMPRISING APHRONS

(75) Inventors: Anthony Fred Mercurio, Rivervale, NJ (US); Derek Alfred Wheeler, Appleton Warrington (GB)

(73) Assignee: Disperse Limited, Warrington (GB)

( * ) Notice: Subject to any disclaimer, the term of this patent is extended or adjusted under 35 U.S.C. 154(b) by 943 days.

(21) Appl. No.: 10/586,328

(22) PCT Filed: Jan. 18, 2005

(86) PCT No.: PCT/GB2005/000162

§ 371 (c)(1),
(2), (4) Date: Jul. 14, 2006

(87) PCT Pub. No.: WO2005/070379

PCT Pub. Date: Aug. 4, 2005

(65) Prior Publication Data

US 2007/0161527 A1    Jul. 12, 2007

(30) Foreign Application Priority Data

Jan. 19, 2004 (GB) ................................. 0401101.1

(51) Int. Cl.
*A61K 7/00* (2006.01)
(52) U.S. Cl. ........................ 510/141; 510/152; 510/153; 510/155; 424/70.1
(58) Field of Classification Search ....................... None
See application file for complete search history.

(56) References Cited

U.S. PATENT DOCUMENTS

| 4,486,333 A | * | 12/1984 | Sebba | ......................... 516/14 |
| 6,165,479 A | | 12/2000 | Wheeler | |
| 2002/0058055 A1 | | 5/2002 | Zecchino et al. | |

FOREIGN PATENT DOCUMENTS

| WO | 9905229 | 2/1999 |
| WO | 03064024 | 8/2003 |
| WO | 03072687 | 9/2003 |
| WO | 2004002436 | 1/2004 |
| WO | WO 2004002436 | 1/2004 |

* cited by examiner

*Primary Examiner*—Necholus Ogden, Jr.
(74) *Attorney, Agent, or Firm*—Dykema Gossett PLLC

(57) ABSTRACT

A solid composition comprising oil core aphrons dispersed in a solid surfactant.

15 Claims, No Drawings

SOLID DISPERSIONS COMPRISING APHRONS

The present invention relates to an aphron dispersion.

An aphron dispersion is also known, especially in its concentrated form, as a polyaphron dispersion and a biliquid foam. This phrase is known, for example, from Sebba, F. (Felix), "Foams and biliquid foams, aphrons", 1987. ISBN: 0471916854. Biliquid foams are known in the art and are described in the following literature references by Sebba: "Biliquid foams", J. Colloid and Interface Science, 40 (1972) 468-474; and "The Behaviour of Minute Oil Droplets Encapsulated in a Water Film", Colloid Polymer Sciences, 257 (1979) 392-396.

U.S. Pat. No. 4,486,333 to Sebba describes a particular method for the preparation of biliquid foams by agitating a hydrogen bonded liquid containing a soluble surfactant to produce a gas foam and intermittently adding to the gas foam a non-polar liquid which is immiscible with the hydrogen bonded liquid, the surfactant-containing hydrogen bonded liquid being selected to provide a spreading coefficient equal to or greater than zero.

Previously aphron dispersions have been added to liquids or foam forming polymers to provide surface coating as disclosed, for example, in WO 99/05229. We have now surprisingly found that certain aphrons can be dispersed in solid or semi-solid surfactants.

Accordingly the present invention provides a solid composition comprising oil core aphrons dispersed in a solid surfactant.

Solid compositions comprising solid surfactants are, of course, well known. They can be used, for example, as soap or syndet bars, deodorants, anti-perspirants sticks, stain removers and many other uses. Such compositions can, for example, clean a variety of surfaces, such as the skin or hair or household or domestic hard or soft surfaces or clothes, or can be used to moisturise the skin, for example to overcome problems of dryness and/or roughness. It is also known to add oils and oil soluble substances to such compositions to alter their function or aesthetics. However, the range of substances which can be added is limited since there has to be a certain degree of compatibility between the surfactant and the oil or oil soluble substance. Furthermore the properties of the surfactant composition may be adversely affected, particularly when relatively large quantities of oil are added. We have unexpectedly found that when oil core aphrons are dispersed in such a composition the original properties of the surfactant remain essentially unchanged or improved. Furthermore we have found that the properties of the oil core, or any compounds contained therein, remains essentially unchanged and is not adversely affected by the surfactant composition. Additionally, the composition has a creamy and luxuriant feel. This can enable a relatively inexpensive soap or syndet bar to have a more expensive feel.

A further problem with the prior art is that only a limited quantity of oil or other hydrophobic substances can be dispersed directly in a solid surfactant. If more than about 2 wt % of such an oil or substance is incorporated in the surfactant the foam is substantially diminished and the surfactant substantially fails to maintain its function and can become virtually unusable. Another problem is that the surfactant often loses its solid processability. Furthermore, higher oil concentrations reduce the integrity of the solid surfactant and its desired use qualities are reduced. In particular it softens and retains water, is consumed in use more rapidly and is aesthetically unpleasing. We have surprisingly found that when oil core aphrons are dispersed in such a surfactant, substantially more oil phase can be incorporated with minimal or reduced foam and/or function suppression. Furthermore the other difficulties discussed above can be alleviated or overcome.

The composition of the present invention is solid and comprises a solid surfactant. Such components are well known. Thus the composition may, for example, be in the form of a solid or gel, preferably one which can simply be held in the hand.

Thus the composition can, for example, be in any form such as a tablet, stick, bar or granules or in any solid form capable of being moulded into these forms.

The solid surfactant may be, for example, a soap, in particular a vegetable based soap or an alkali metal salt of a long chain fatty acid. Suitable long chain fatty acids contain from 8 to 24 carbon atoms in the long chain, especially 12 to 18 carbon atoms. A preferred soap is a stearate such as sodium stearate.

The solid surfactant may also be a synthetic surfactant, for example an anionic, cationic, amphoteric, nonionic or zwitterionic surfactant. Examples of suitable surfactants are sodium cocoate, sodium tallowate, sodium palm kernelate, sodium palmitate, triethanolamine stearate, sodium cocoyl isethionate, sodium isethionate, sodium dodecyl benzene sulfonate and sodium cocoglyceryl ether sulfonate.

The surfactants can be used singly or in a combination of two or more. Further surfactants may also be added. In particular a soap and a synthetic surfactant may be used together, for example to form a "combar".

The composition of the present invention also comprises oil core aphrons. The internal phase of the aphrons is oil based, that is to say hydrophobic. Preferred oil cores comprise an oil, ester, an extract (for example from a vegetable or plant) or other water insoluble liquid or mixture thereof. Such oil cores may, for example, confer an emollient, moisturising, conditioning or other cosmetic, pharmaceutical or pest control benefit to the skin or hair. Suitable oil phases are, for example, oils which are liquid at room temperature (e.g. 20° C.) such as, for example, one or more selected from a cyclomethicone, dimethicone, dimethiconol, dimethicone copolyol, an emollient ester such as isopropyl stearate, lanolate, myristate or palmitate, or octyl palmitate, a glyceride such as avocado oil, coconut oil, soybean oil or sunflower oil, or a caprylic/capric triglyceride, a lanolin oil, mineral oil or natural oil, or oleyl alcohol, or any other oil known to be used in emulsions for whatever purpose. Also included in the definition of oil are water insoluble solvents such as hexane, toluene, benzene, kerosene, diesel oil and other like solvents and water-insoluble organic liquids. If necessary or desired, solvents and/or freezing point depression aids may be added, especially to ensure that the oils remain liquid at room temperature.

The aphron dispersion may be prepared by standard techniques known in the art, for example by those indicated herein.

Methods of producing biliquid foams are described in, for example, U.S. Pat. No. 4,486,333, U.S. Pat. No. 6,165,479 or WO 99/05229. These involve the preliminary formation of a gas foam in order to provide a sufficiently large surface area on which the biliquid foam can subsequently be formed. It has been found that the prior formation of a gas foam is not required to manufacture a stable biliquid foam, provided that a suitable stirring mechanism is provided in the manufacturing vessel.

Such an apparatus comprises a tank provided with a stirrer in which the stirrer blade breaks the interface between the liquid and air and provides low shear mixing throughout the whole of the volume of the biliquid foam throughout the whole of the production process. A delivery device is provided through which the internal phase of the dispersion, which in this case comprises at least two liquids, is delivered to the tank. The design of the delivery device is such that the rate of addition of the internal phase fluid can be controlled and varied during the production process.

A feature of the production process is that the internal phase is added to the stirred external phase slowly at first until sufficient droplets have been formed to constitute a large, additional surface area for the more rapid formation of new droplets. At this point, the rate of addition of the internal phase may be increased.

The production process preferably comprises the elements disclosed in WO 03/072687 and/or WO 03/064024.

It will be understood by those skilled in the art that other manufacturing methods for the aphron dispersion may be used, as appropriate.

The internal oil phase and/or the external phase in the remainder of the composition of the present invention may also comprise, for example, other components or additives. Thus either or both phases may, for example, comprise a further surfactant, such as a liquid surfactant, a fragrance, colourant, natural or synthetic therapeutic agent, skin conditioner, a moisturiser, an anti-bacterial or anti-fungal agent, an opacifier, an oil or fat, a sugar, a pH adjuster, a pigment, a foam builder, a pest control agent such as an insect repellent or a physiologically active, oil-soluble material. A suitable additive is, for example, at least one of the anti-bacterial agents benzoyl peroxide, sulphur or a resorcinol such as triclosan or triclocarban, a vegetable oil such as olive oil, an acidic pH adjuster such as citric acid or lactic acid, sucrose, glycerine, the moisturiser sodium lauryl isethionate or the opacifier titanium dioxide. The external phase may also comprise one or more solubilisers, dispersing agents and/or freeze-thaw protectors, for example solvents such as water, an alcohol and/or a glycol. It is particularly preferred that the external phase comprises water, or a mixture of water and an alcohol, optionally together with a glycol.

The composition of the present invention may, as indicated above, comprise a relatively large amount of oil core aphrons. Preferably the composition comprises from 0.1 to 20 wt % oil core aphrons, more preferably from 0.5 to 15 wt % of the oil core aphrons, especially 2.5 or 5 to 15 wt % of the oil core aphrons.

The composition may, for example, be in the form of a cosmetic, toiletry, pharmaceutical or household product. It may take the form of a stick, tablet, bar or granules. Preferably the composition is in the form of a soap or syndet bar or a mixture thereof, a deodorant or anti-perspirant stick or a stain remover.

The compositions of the present invention may be formed simply by incorporating the oil core aphrons during the manufacturing process of the composition. Thus, for example, an oil core aphron dispersion can simply be added into the base composition, for example comprising the surfactant and any other components such as fragrance or colourant, and then the composition mixed and extruded before being cut and stamped to a final shape. Alternatively a transparent or translucent soap or syndet bar can be produced by a heat-melt-pour method, and the aphrons incorporated in the composition before it is poured.

The present invention will now be further described with reference to the following examples:

EXAMPLES

Example 1

Preparation of a Stick Deodorant

An aphron dispersion A was prepared from:

| | |
|---|---|
| Peach Kernel Oil | 30.0 parts |
| Avocado Oil | 30.0 parts |
| Diisopropyl Adipate | 29.1 parts |
| Surfactant | 1.0 part |
| Water | 9.9 parts. |

Various non-alcoholic stick deodorants were then prepared from:

| | |
|---|---|
| Propylene Glycol | 66.0 parts |
| Water | 20.0 parts |
| Cocamide MIPA | 5.0 parts |
| Sodium Stearate | 8.0 parts |
| Preservative | 1.0 part |
| Biliquid Foam A | 0.5-10 parts |

The propylene glycol, water, Cocamide MIPA and sodium stearate were mixed together and heated to 75° C. The preservative was then added and the mixture mixed until a clear solution was obtained. After cooling to 65° C. the aphron dispersion was added. The temperature was maintained at 65° C. while the mixture was filled into containers and allowed to set.

Example 2

Preparation of a Stick Deodorant

Various alcoholic stick deodorants were then prepared from the following compositions using the method of Example 1:

| | |
|---|---|
| Alcohol SDA-40 | 66.0 parts |
| Water | 20.0 parts |
| Cocamide MIPA | 5.0 parts |
| Sodium Stearate | 8.0 parts |
| Preservative | 1.0 part |
| Biliquid Foam A | 0.5-10 parts |

Example 3

Preparation of a Syndet Soap

An aphron dispersion B was prepared of aphrons containing sweet almond oil.

In a blender 85 to 99.5 parts of syndet soap base chips were added, and mixed thoroughly with 0.5 to 15 parts respectively of aphron dispersion B. The mixture was passed through a 3 roll mill, and then milled a second time. The mixture was then passed through a plodder and pressed into bars.

Soap bars were also prepared in the same manner but by substituting the syndet soap base by a glycerine soap base or a hard milled soap base.

It was found that all the soaps maintained their soap lather and aesthetic properties even when the oil is incorporated in a relatively large amount.

Example 4

Preparation of a Glycerin Soap

In a vessel 85 to 99.5 parts of glycerin soap chips were added and melted until a clear solution was obtained. 0.5 to 15 parts respectively of aphron dispersion B were then added and mixed into the solution until the mixture was uniform. The mixture was then poured into moulds and cooled.

It was again found that all the soaps maintained their soap lather and aesthetic properties even when the oil is incorporated in a relatively large amount.

The invention claimed is:

1. A solid composition comprising oil core aphrons dispersed in a solid surfactant.

2. A composition according to claim 1 wherein the surfactant comprises at least one soap.

3. A composition according to claim 2 wherein the soap is a vegetable based soap or an alkali metal salt of a fatty acid containing 12 to 18 carbon atoms in the fatty chain.

4. A composition according to claim 3 wherein the soap is sodium stearate.

5. A composition according to claim 1, wherein the surfactant comprises at least one synthetic surfactant.

6. A composition according to claim 5 wherein the synthetic surfactant is sodium cocoate, sodium tallowate, sodium palm kernelate, sodium palmitate, triethanolamine stearate, sodium cocoyl isethionate, sodium isethionate, sodium dodecyl benzene sulfonate, sodium cocoglyceryl ether sulfonate or a mixture thereof.

7. A composition according to claim 1 which comprises 0.1 to 20 wt % of the oil core aphrons.

8. A composition according to claim 1 which also comprises water and/or an alcohol.

9. A composition according to claim 1 which also comprises a glycol.

10. A composition according to claim 1 wherein the oil core comprises an oil, ester or other water insoluble liquid or a mixture thereof which confers an emollient, moisturising, cleansing, conditioning or other cosmetic, personal care or pharmaceutical benefit to the skin, hair or a fabric.

11. A composition according to claim 1 wherein the oil core comprises a fragrance, a colourant, a natural or synthetic therapeutic agent, a skin conditioner, an anti-bacterial or anti-fungal agent, a pest control agent or a physiologically active, oil-soluble component.

12. A composition according to claim 1 which further comprises at least one of a further surfactant, a fragrance, a colourant, a natural or synthetic therapeutic agent, a skin conditioner, a moisturizer, an anti-bacterial or anti-fungal agent, an opacifier, an oil or fat, a sugar, a pH adjuster, a pigment, a foam builder on a pest control agent.

13. A composition according to claim 1 which is in the form of a stick, tablet, bar or granules.

14. A composition according to claim 1 which is a cosmetic, toiletry, household or pharmaceutical product.

15. A composition according to claim 1 which is a soap or a syndet bar, a combar, a deodorant, an antiperspirant stick or a stain remover.

\* \* \* \* \*